United States Patent [19]
Bryerton, Sr.

[11] Patent Number: 5,509,146
[45] Date of Patent: Apr. 23, 1996

[54] EAR MUFFS

[76] Inventor: Donald Bryerton, Sr., 207 13th Ave., Box 297, Sylvan Beach, N.Y. 13157

[21] Appl. No.: 163,714

[22] Filed: Dec. 9, 1993

[51] Int. Cl.⁶ ........................................ A42B 1/06
[52] U.S. Cl. ........................................ 2/209; 2/2
[58] Field of Search .................. 2/2, 209, 423, 2/DIG. 11; 128/857, 864, 865, 866, 867, 868; D29/112

[56] References Cited

U.S. PATENT DOCUMENTS

| | | | |
|---|---|---|---|
| D. 149,150 | 3/1948 | Schwartz | D3/13 |
| D. 166,399 | 4/1952 | Lattuca | D3/2 |
| 170,942 | 12/1875 | Edgar. | |
| D. 206,256 | 11/1966 | Boyer | D3/13 |
| D. 215,138 | 9/1969 | Mackey | D2/3 |
| D. 254,876 | 5/1980 | Reitenga et al. | D2/259 |
| D. 311,074 | 10/1990 | Scott et al. | D29/19 |
| D. 346,882 | 5/1994 | Bryerton, Sr. | D29/112 |
| 2,314,782 | 3/1941 | Goretsky | 2/209 |
| 2,883,672 | 4/1959 | Hornickel et al. | 2/209 |
| 4,669,129 | 6/1987 | Chance | 2/209 |
| 4,674,134 | 6/1987 | Lundin | 2/209 |
| 4,905,322 | 3/1990 | Aileo et al. | 2/209 |

Primary Examiner—Diana Biefeld
Attorney, Agent, or Firm—Trapani & Molldrem

[57] ABSTRACT

Ear muffs having an adjustable head band with ear pieces resembling a racing slick or monster truck tire. The ear pieces include removable hubcap discs on the outwardly facing sides thereof on which indicia may be applied in the nature of a race driver's name or the name of the racing establishment, for example. Ear cushions having a noise muffling material are removably attached to the inwardly facing sides of the tire ear pieces.

20 Claims, 2 Drawing Sheets

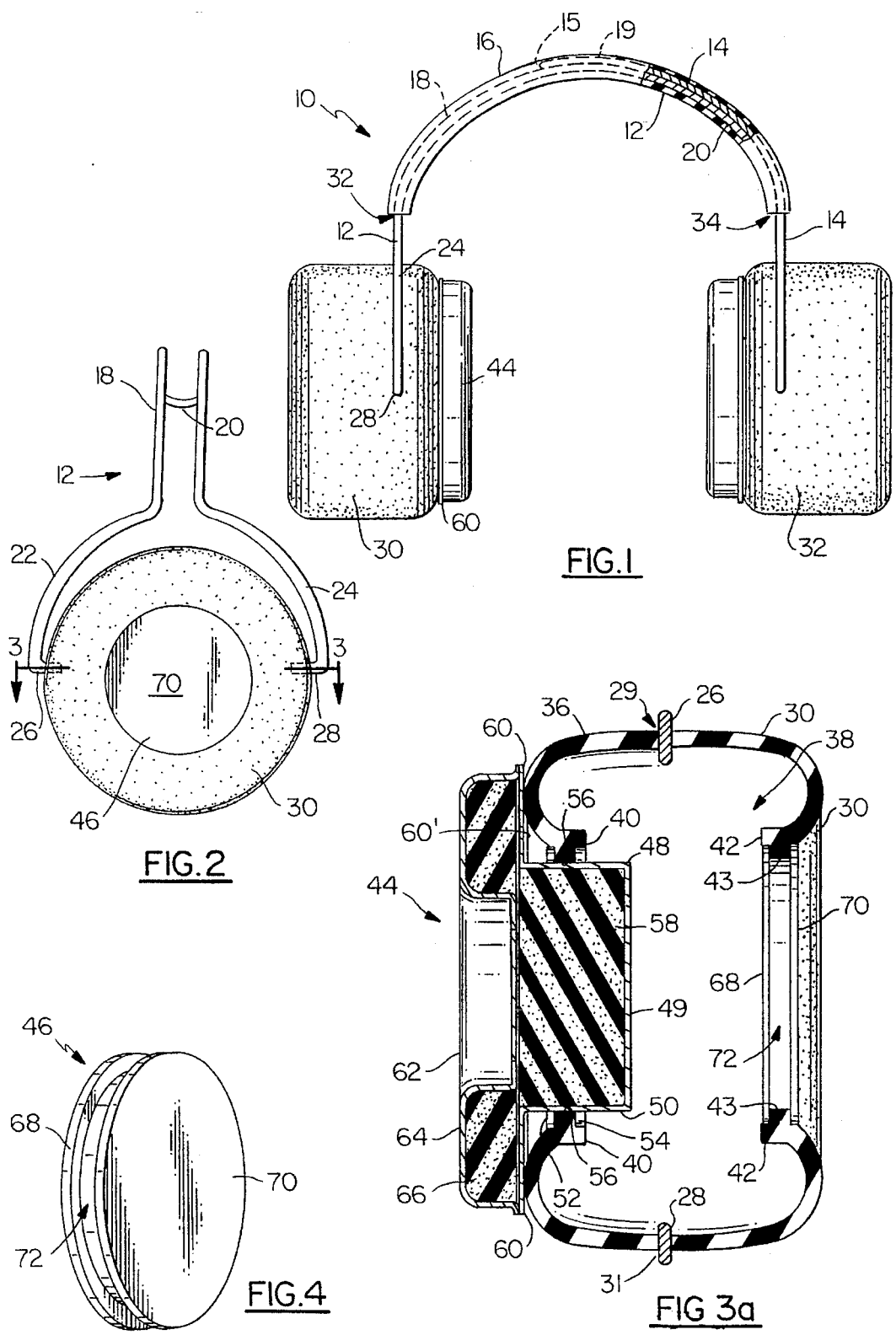

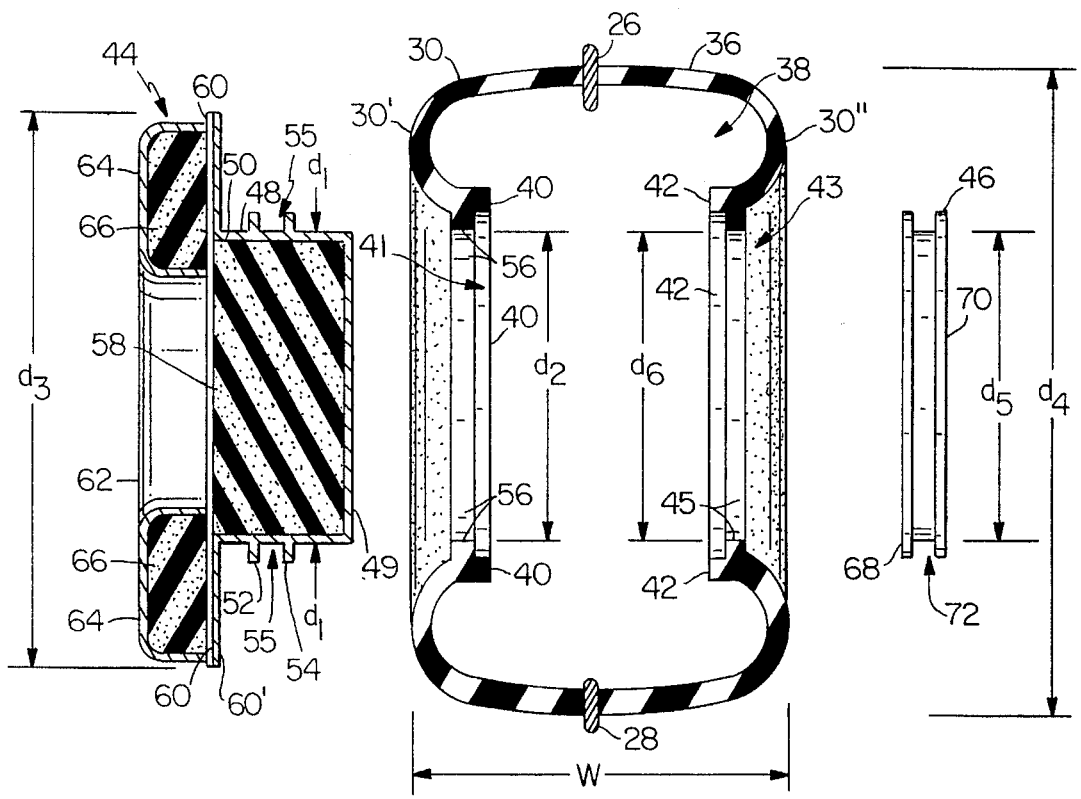
FIG.3b
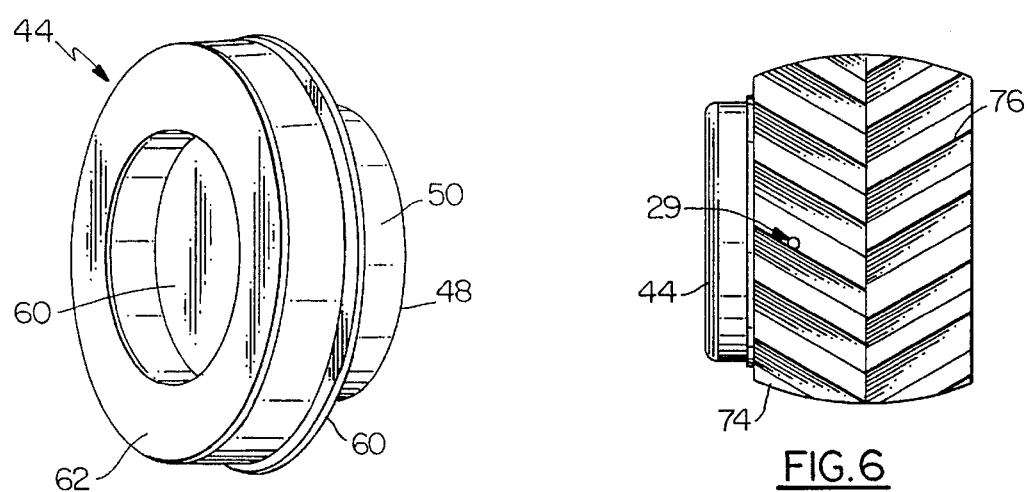
FIG.5
FIG.6

EAR MUFFS

BACKGROUND OF THE INVENTION

This invention relates to ear muffs which are worn upon the head of a person about the ears and, more particularly, to novel and unique ear muffs which have ear pieces made to simulate a tire. In the preferred embodiments of the invention, the tire ear piece simulates a racing stick and, alternatively, a so-called "monster" truck tire.

At sporting events such as automobile races and truck/tractor competitions, the noise created by the vehicles can sometimes be very loud especially to those located near the track or other competition area. It is well known that the noise can be physically damaging to the ears besides being a source of great discomfort for many people. It is also known that there exist ear muffs which are constructed to protect the ears from such loud noises such as those seen worn by an auto racer's pit crew who are located in the highest noise areas. However, these ear muffs are for noise deadening purposes only, and little or no consideration is given to attractive design features.

It is also well known that souvenir items sold at these type of sporting events are a major source of income for both the participants (i.e., drivers/sponsors) and the sport establishment owners. Many of the souvenir items are also meant to show the fans' support of a particular, driver and/or sport establishment. The present invention addresses the noise level problem at these types of sporting events, and also provides an item which lends itself toward driver and/or establishment support thereby being available as a souvenir item to be purchased and worn by supporting fans.

SUMMARY OF THE INVENTION

It is therefore a principle object of the present invention to provide noise-reducing ear muffs for wearing at automobile/truck/tractor sporting events which may be purchased as a unique souvenir item.

It is another object of the present invention to provide ear muffs having ear pieces which simulate a tire (e.g., a racing slick or monster truck tire).

It is a further object of the present invention to provide ear muffs of the above type which have removable ear pieces such that different ear piece designs may be substituted for each other as desired.

It is yet another object of the present invention to provide ear muffs of the above type which have printable portions thereof for imprinting the name and/or logo of the driver/establishment the fan wishes to support.

It is still a further object of the present invention to provide ear muffs of the above type in which the printable portions are separately removable from its respective ear piece and thus interchangeable with other ear pieces.

It is yet a further object of the present invention to provide ear muffs which are comfortable to wear.

Other objects will in part be obvious and in part appear hereinafter.

In accordance with the foregoing objects, the invention comprises a set of ear muffs having two ear pieces which simulate a tire. In the two preferred embodiments set forth below, the tire ear pieces simulate a race car racing slick tire and a monster truck tire, although it is understood that a potentially infinite number of different tire designs could be used with the present invention.

The ear muffs include an adjustable head band with two identical tire ear pieces being removably attachable to either end of the headband. The tire ear pieces are formed hollow from any suitable material such as rubber or plastic, for example, (preferably a resilient material) and have a central opening which extends laterally entirely through the tire. An ear cushion which includes a noise muffler is removably attached to the perimeter of the inwardly facing opening of each tire ear piece. A planar, circular disc serves as the tire "hubcap" and is removably attached to the perimeter of the outwardly facing opening of each tire ear piece. The outwardly facing surface of the attached disc presents a smooth, circular surface area at the center of the tire ear piece on which any desired indicia may be imprinted, such as the name and/or logo of a driver or the track establishment. The disc may also be left blank for the consumer to apply a logo and/or name of his/her choice at a later time. Also, since the discs are removable from the tire ear piece, different discs having different names and/or logos may be substituted by the consumer as desired. Therefore, the consumer may purchase one set of the ear muffs and change the hubcap discs whenever desired, for example, when attending different racing events.

BRIEF DESCRIPTION OF THE DRAWINGS

FIG. 1 is a fragmented, front elevational view of the ear muffs with racing slick tire ear pieces attached thereto;

FIG. 2 is a side elevational view of one of the ear pieces of FIG. 1 with a respective ear piece attachment band attached thereto;

FIG. 3a is a cross-sectional view as taken along the line 3—3 in FIG. 2;

FIG. 3b is the view of FIG. 3a showing the ear cushion and hubcap disc removed and in spaced relation to the tire ear piece;

FIG. 4 is a perspective view of the circular hubcap disc;

FIG. 5 is a perspective view of the ear cushion and noise muffler; and

FIG. 6 is an elevational view of a truck tire ear piece which may be interchanged with the racing slick tire ear pieces seen attached to the head band in FIGS. 1–3.

DETAILED DESCRIPTION

Referring now to the drawings, there is seen in FIG. 1 a set of the inventive ear muffs indicated generally by the reference numeral 10. Ear muffs 10 include a one-size-fits-all head band comprising first and second identical ear piece attachment bands 12 and 14 connected together by an arcuate shaped connecting piece 16. Attachment bands 12 and 14 are preferably formed of tempered spring steel and connecting piece 16 is preferably formed of plastic.

Although the discussion below relates mostly to only one side of ear muffs 10 (the side including tire ear piece 30 and attachment band 12) for purposes of brevity, it is understood that the other side of muffs 10 (including tire ear piece 32 and attachment band 14) is identical in structure to and thus a mirror image of the side having tire ear piece 30.

As seen in FIG. 2, ear piece attachment band 12 is formed from a single piece of bent spring steel and includes an arcuate portion 18 having a curved end 20, and diverging shoulder segments 22 and 24 which have inwardly directed, terminal ends 26 and 28, respectively. Terminal ends 26 and 28 removably insert into apertures 29 and 31 formed in the tire ear pieces 30, respectively (see also FIGS. 3a and b).

Referring again to FIG. 1, connecting piece 16 is formed hollow and includes openings 32 and 34 at opposite ends thereof wherein curved ends 20 and 15 of attachment bands 12 and 14 are inserted, respectively. Arcuate portions 18 and 19 of attachment pieces 12 and 14, respectively, are cooperatively shaped to frictionally slide back and forth against each other within connecting piece 16 thereby allowing the distance between tire ear pieces 30 and 32 to be quickly and easily adjusted as needed.

As seen best in FIGS. 3a and b, tire ear piece 30 is similar in appearance to a racing slick tire and has a smooth outer, cylindrical surface 36 and a hollow center 38. Tire ear piece 30 is generally longitudinally symmetrical with the perimeters of the opposite sides of surface 36 bending inwardly towards each other at edges 40 and 42 thereby defining inner and outer, circular openings 41 and 43 wherein ear cushion 44 and hubcap disc 46 are removably inserted, respectively.

More particularly, ear cushion 44 is seen in FIGS. 3a and b and 5 to include a rigid, cylindrical cup portion 48 with the outer cylindrical surface 50 thereof including first and second, parallel, annular flanges 52 and 54 forming a groove 55 therebetween. In this respect, cup portion 48 has a diameter $d_1$ which is substantially the same as the diameter $d_2$ of the inner opening in tire ear piece 30 at flange 56 providing a snug fit between the cup portion 48 and tire ear piece 30. Insertion and removal of cup portion 48 from tire ear piece 30 is facilitated by virtue of the resiliency of tire ear piece 30. An annular flange 56 is formed on the inner surface of edge 40 and is removably inserted into groove 55 of cup portion 48 upon inserting cup portion 48 within opening 41 of tire ear piece 30. Cup portion 48 is filled with a noise-muffling padding material 58 which will muffle, but not completely drown out, the noise at the track or other sporting event. This padding 58 may be polyurethane foam, for example.

A planar, circular middle wall 60 attaches to the perimeter of cup portion 48 opposite bottom surface 49 and lies in a plane perpendicular to cylindrical surface 50 thereof. The diameter $d_3$ of middle wall 60 is slightly smaller than the diameter $d_4$ of cylindrical surface 36 of tire ear piece 30 with portions of wall 60 lying in contacting, abutting contact with the inner side 30' of tire ear piece 30 when ear cushion 44 is fully inserted within the opening 41. In this respect, a pressure-sensitive adhesive 60' may be applied to the inner surface of wall 60 to assist maintaining middle wall 60 against tire ear piece 30. An annular ear pad 62 is affixed in covering relation to the outer surface of wall 60 and comprises a soft vinyl outer cover 64 filled with a soft, resilient padding material 66 (e.g., polyurethane foam). When ear muffs 10 are put on the head, the ear pads 62 of each tire ear piece 30 and 32 should lay about and against the ears.

Referring now to the outwardly facing radially outer annular sides 30" of tire ear pieces 30 and 32, it is seen in FIGS. 2–4 that hubcap disc 46 is provided which is removably inserted within the outwardly facing opening 43 or central hub portion of tire ear piece 30 defined by edge 42. Disc 46 is termed a "hubcap" disc herein since it resembles and is in a position similar to an actual tire hubcap. Hubcap disc 46 includes first and second, circular surfaces 68 and 70 which lie in spaced, parallel planes. An annular groove 72 is formed between surfaces 68 and 70 and has a diameter $d_5$ substantially the same as the diameter $d_6$ of the outer opening 43 in tire ear piece 30 defined by the annular flange 45 extending along the inwardly facing surface of edge 42. As such, hubcap disc 46 may be removably attached to tire ear piece 30 by inserting flange 45 within groove 72. Again, this is easily accomplished due to the resilient nature of the material from which the tire ear pieces 30 and 32 are made.

Hubcap disc 46 is rigid and is preferably formed from plastic which provides a smooth surface adapted to receive indicia thereon. As mentioned previously, this may be the name of a driver, the name/logo of a sports establishment, or the name/logo of a sporting event, etc. The indicia is applied to the outwardly facing surface 70 of hubcap disc 46 for clear viewing by others, and may be printed directly thereon by screenprinting, with marker or paint, or a removable decal may be used which would allow different decals to be applied to surface 70 as desired. In any event, the hubcap discs 46 themselves are removable from tire ear piece 30 in the manner described above so that the consumer may switch between many different discs 46 having different names/logos imprinted thereon, or blank discs so that the consumer may apply any desired indicia thereon him/herself.

It will be appreciated that tire ear pieces 30 and 32 simulate the actual appearance of a racing slick. Referring to FIG. 3b, it is seen the maximum width w of tire ear piece 30 is approximately half of the diameter $d_4$ of cylindrical surface 36.

Referring lastly to FIG. 6, an ear piece 74 is provided which simulates a truck tire including treads 76. The structure of truck tire ear piece 74 is essentially the same as racing slick tire ear pieces 30 and 32 with the only major difference being the presence of treads 76 to give the appearance of a truck tire as opposed to a racing slick which has no treads. Thus, it is envisioned that ear muffs having racing slick ear pieces 30 and 32 would be offered to fans at a race track while ear muffs having truck tire ear pieces 74 would be offered to fans at a truck race/competition (e.g., the popular "monster" truck competitions). It will be appreciated that the interchangability of all parts of ear muffs 10 provide for a versatile and highly desirable souvenir item.

While the foregoing description has related to preferred embodiments of the invention, it will be understood that various modifications may be made thereto without departing from the full spirit and scope of the invention as defined by the claims which follow.

What is claimed is:

1. Noise-suppressing ear muffs comprising:
    a) a headband having first and second, laterally spaced ear piece attachment bands;
    b) first and second ear pieces in the shape of automotive tires, each having inner and outer opposite circular sides and a cylindrical outer surface extending therebetween about the circumferences of said inner and outer circular sides, said outer side of each ear piece having a radially outer annular tire portion and a central hub portion;
    c) means removably attaching said first and second ear pieces to said first and second ear piece attachment bands, respectively, with said inner sides of said ear pieces facing inwardly toward each other and said outer sides of said ear pieces facing outwardly away from each other;
    d) first and second circular discs each in the shape of a hubcap of an automotive tire; and
    e) means removably attaching said first and second discs into the central hub portion of said outer sides of said first and second ear pieces, respectively, with said discs lying in planes perpendicular to a respective said cylindrical surface.

2. The invention according to claim 1 wherein said means removably attaching said first and second discs to said outer sides of said first and second ear pieces, respectively, comprises:

a) first and second circular openings formed in said outer sides of each of said first and second ear pieces, respectively;

b) first and second annular flanges encircling the perimeters of said first and second circular openings, respectively; and c) first and second annular grooves encircling the perimeters of said first and second discs, respectively, between said first and second planar surfaces thereof, said first and second annular grooves having substantially the same diameters as said first and second openings at said first and second flanges, said first and second flanges being removably insertable into said first and second grooves, respectively, with one of said first and second planar surfaces facing outwardly and exposed to receive printed indicia thereon.

3. The invention according to claim 2 and further comprising first and second ear cushions attached to said inner sides of said first and second ear pieces, respectively.

4. The invention according to claim 3 and further comprising means removably attaching said first and second ear cushions to said inner sides of said first and second ear pieces, respectively.

5. The invention according to claim 4 wherein said first and second ear cushions include first and second cylindrical portions having respective first and second cylindrical surfaces, respectively, and wherein said means removably attaching said first and second ear cushions to said inner sides of said first and second ear pieces comprises:

a) third and fourth circular openings formed in said inner sides of said first and second ear pieces, respectively;

b) third and fourth annular flanges encircling the perimeters of said third and fourth circular openings, respectively;

c) third and fourth annular grooves encircling said first and second cylindrical surfaces of said first and second ear cushions, respectively, said third and fourth grooves having substantially the same diameters as said third and fourth flanges, said third and fourth flanges being removably insertable into said third and fourth grooves, respectively.

6. The invention according to claim 5 wherein said first and second ear cushions further include first and second, annular ear pads attached to said first and second cylindrical portions, respectively, said first and second ear pads lying against said inner sides of said first and second ear pieces upon removably attaching said first and second ear cushions to said inner sides of said first and second ear pieces, respectively.

7. The invention according to claim 6 wherein said first and second cylindrical portions of said first and second ear cushions each have an internal cavity containing a noise-muffling material.

8. The invention according to claim 7 wherein said noise-muffling material is polyurethane foam padding.

9. The invention according to claim 6 wherein said first and second ear pads are formed of a resilient material.

10. The invention according to claim 9 wherein said resilient material is a polyurethane core covered by flexible vinyl sheeting.

11. The invention according to claim 1 wherein said means removably attaching said first and second ear bands to said first and second ear piece attachment pieces comprises:

a) elongated first and second, laterally spaced shoulder segments extending from said first and second ear piece attachment pieces, respectively, and having respective first and second, inwardly projecting terminal end portions; and b) first and second diametrically opposite apertures formed through each of said first and second cylindrical surfaces of said first and second ear pieces, respectively, said first and second terminal end portions of said first and second shoulder segments being removably insertable into said first and second apertures of each of said first and second ear pieces, respectively.

12. The invention according to claim 1, said first and second ear pieces further comprising noise-muffling means which will muffle, but not completely drown out, noise at a track or sporting event.

13. The invention according to claim 1, wherein the central hub portions of said outer sides each have a circular opening having an annular flange, and the first and second discs each have an annular groove which removably seats the respective annular flange.

14. Noise-suppressing ear muffs comprising:

a) a headband having first and second, laterally spaced ear piece attachment bands; and b) first and second ear pieces attached to said first and second ear piece attachment bands, respectively, said first and second ear pieces each being formed as a hollow shell having an outer cylindrical surface of a predetermined diameter ($d_4$) and width (w), said ear pieces each further having opposite inner and outer, circular sides with said cylindrical surface lying between said inner and outer circular sides, said inner circular sides facing toward each other on said headband and said outer circular sides facing away from each other on said headband;

wherein said first and second ear pieces include first and second resilient annular ear pads attached to said inner circular sides thereof, respectively, and further comprising means removable attaching said first and second ear pads to said first and second ear pieces, respectively, and said removable attachment means comprise:

a) first and second circular openings formed in said inner circular sides of said first and second ear pieces, respectively;

b) first and second annular flanges attached to and encircling the perimeters of said first and second circular openings;

c) first and second cylindrical cup portions attached to said first and second ear pads, respectively, and having diameters substantially the same as the diameters of said first and second circular openings at said first and second flanges, respectively;

d) first and second annular grooves formed on and encircling said first and second cylindrical cup portions, respectively, said first and second flanges of said first and second circular openings being engaged within said first and second annular grooves of said first and second cylindrical cup portions upon removably attaching said first and second cylindrical cup portions to said first and second ear pieces in said first and second circular openings thereof, respectively.

15. The invention according to claim 14 wherein said first and second cylindrical cup portions each have an internal cavity containing a noise-muffling material.

16. The invention according to claim 15 wherein said noise-muffling material is polyurethane foam.

17. The invention according to claim 14 wherein said first and second ear pieces include first and second, circular, planar discs attached to said outer circular sides thereof, respectively.

18. The invention according to claim 17 and further comprising means removably attaching said first and second discs to said first and second ear pieces, respectively.

19. The invention according to claim 18 wherein said removable attachment means comprises:
 a) first and second circular openings formed in said outer circular sides of said first and second ear pieces, respectively;
 b) first and second annular flanges attached to and encircling the perimeters of said first and second circular openings;
 c) first and second annular grooves formed on and encircling said first and second discs, respectively, said first and second flanges of said first and second circular openings being engaged within said first and second annular grooves of said first and second discs upon removably attaching said first and second discs to said first and second ear pieces in said first and second circular openings thereof, respectively, with said first and second discs lying in a plane perpendicular to said outer cylindrical surface of a respective one of said first and second ear pieces.

20. Noise-suppressing ear muffs comprising:
 a) a headband having first and second, laterally spaced ear piece attachment bands; and
 b) first and second ear pieces attached to said first and second ear piece attachment bands respectively, said first and second ear pieces each being formed as a hollow shell having an outer cylindrical surface of a predetermined diameter ($d_4$) and width (w), said ear pieces each further having opposite inner and outer, circular sides with said cylindrical surface lying between said inner and outer circular sides, said inner circular sides facing toward each other on said headband and said outer circular sides facing away from each other on said headband; wherein said outer circular sides each have a central circular opening having an annular flange, and further comprising first and second circular discs each having an annular circumferential groove which removably seats an associated one of the annular flanges, so that said discs are removably held in place in said first and second ear pieces.

\* \* \* \* \*